United States Patent [19]
Herrmann

[11] Patent Number: 5,885,223
[45] Date of Patent: Mar. 23, 1999

[54] PROCESS AND DEVICE FOR ASSESSING ELECTROENCEPHALOGRAMS

[76] Inventor: Christoph Herrmann, Wettinerstrasse 16, Leipzig, Germany, 04105

[21] Appl. No.: 973,310
[22] PCT Filed: May 29, 1996
[86] PCT No.: PCT/EP96/02309
  § 371 Date: Dec. 1, 1997
  § 102(e) Date: Dec. 1, 1997
[87] PCT Pub. No.: WO96/38082
  PCT Pub. Date: Dec. 5, 1996

[30] Foreign Application Priority Data

May 31, 1995 [DE] Germany ............ 195 19 267.2

[51] Int. Cl.$^6$ .................................... A61B 5/048
[52] U.S. Cl. ............................................ 600/544
[58] Field of Search .................. 600/544, 545, 600/547, 558; 128/898

[56] References Cited

U.S. PATENT DOCUMENTS 3,760,796  9/1973  Baessler et al. .
4,579,125  4/1986  Strobl et al. .
4,610,259  9/1986  Cohen et al. .
4,776,345  10/1988 Cohen et al. .
5,363,858  11/1994 Farwell ......................... 600/544
5,458,117  10/1995 Chamoun et al. ............. 600/547
5,467,777  11/1995 Farwell ......................... 600/544

FOREIGN PATENT DOCUMENTS

1192612  5/1970  United Kingdom .

Primary Examiner—George Manuel
Attorney, Agent, or Firm—Jacobson, Price, Holman & Stern, PLLC

[57] ABSTRACT

In order to facilitate assessment of the activity of the brain by the medical practitioner, the description relates to a process for assessing electrically recorded brain activity in which a signal taken from a skull over a predetermined period at a predetermined scanning frequency is converted into a sequence of data words from which the amplitudes and the frequencies relating to each amplitude are extracted in a computer system in a predetermined pattern in such a way that intermediate data words are formed, each of which represents an amplitude and is stored under a store address determined by the frequency allocated to the intermediate data word, and those maximum intermediate data words of all of them are determined which are a relative maximum and a mean is drawn at each frequency from the maximum intermediate data words and all means with the relevant frequency are taken to a display device for representation in a frequency/amplitude curve.

19 Claims, 9 Drawing Sheets

PROCESS AND DEVICE FOR ASSESSING ELECTROENCEPHALOGRAMS

The invention relates to a method for evaluating electrical brain current signals picked off from the top of the skull over a given time interval, and to a device which is suitable for this purpose.

German Laid-Open Specification 15 41 173 discloses a method for information compression of electroencephalograms, time intervals being determined for which the upper and lower curve inversion point of a brain current signal is the governing factor. German Laid Open Specification 22 47 572 discloses a method and an apparatus for automatic analysis of brain current signals, in which method a signal is produced from an analog EEG signal over a given time interval, that [sic] relates to the frequency of the EEG signal. These methods for brain current representation have the disadvantage that they do not provide the doctor with any cohesive, simple, easily viewed information about the detected brain activity.

EP-A-0 150 125 discloses a method for evaluating electrically detected brain activity, in which a signal which is picked off from the top of the skull over a predetermined time interval is converted at a predetermined sampling frequency into a sequence of data words from which the amplitudes as well as the frequency associated with each amplitude are extracted in accordance with a predetermined scheme, for example a Fourier transformation, in an arithmetic unit, in such a manner that intermediate data words are formed, each of which represents an amplitude and is stored at a memory address. Furthermore, mean values are formed from the intermediate data words in the known apparatus, and all the mean values are passed, with the associated frequency, to an indicator device for display on a frequency/amplitude graph.

The invention is thus based on the object of making it easier for the doctor to assess brain activity.

To this end, the invention provides that the signal is converted at a given sampling frequency into a sequence of data words from which the amplitudes and the frequency associated with each amplitude are extracted in accordance with a predetermined scheme (Fourier transformation or the like) in an arithmetic unit, in such a manner that intermediate data words are formed, each of which represents an amplitude and is saved at a memory address which is governed by the frequency associated with the intermediate data word, furthermore, of all the intermediate data words, those maximum intermediate data words being determined which are a relative maximum, and in such a manner that a mean value is formed from the maximum intermediate data words for each frequency and all the mean values are passed with the associated frequency to an indicating device for display using a frequency/amplitude graph.

There is thus a so-called sum spectrum for each recorded track on the electroencephalogram, from which the doctor can use the position of the maxima for the individual frequencies to draw conclusions about brain activity directly. The basic activity and any pathological activity of the brain activity can thus be taken from a single curve profile, and can easily be assessed medically.

In a preferred refinement of the invention, in order to form the mean value, the sum of the maximum intermediate data words present per frequency is multiplied by the number of said words and is divided by a given reference variable.

Furthermore, it is recommended that, with the time interval being subdivided into a number of time units, the extraction be carried out for each time unit (sampling second), the intermediate data words formed for each time unit being saved at memory addresses which are defined unambiguously for the time unit by the frequency associated with the intermediate data word, and the number of time units in the time interval being chosen as the reference variable. The mean value data words fed to the indicating device (30) are preferably passed via a low-pass filter.

For deeper evaluation by the doctor and as a continuation of the invention, it is possible to determine from the mean value data words those which are a relative minimum, the frequency associated with each minimum mean value data word being fed to the indicating device for separate display. A frequency drift graph can be obtained from this, if the frequencies of the maximum intermediate data words in each time unit are determined and are passed to the indicating device.

A single graph is thus produced for one record track of the EEG, in which the doctor can immediately see the times during the scan, and the frequencies, at which activity maxima have occurred. This considerably simplifies medical evaluation, in comparison with conventional representation.

Finally, the invention makes it easy to check, for example, the Berger effect if, for each time unit, all the intermediate data words within a frequency interval are passed to the indicator unit for an amplitude drift display, the frequency interval being defined by the frequency difference between second two minimum mean value data words.

A device as specified in claim 10 is particularly suitable for carrying out the described method.

In addition, preferred embodiments of the invention are contained in the dependent claims.

The invention will be described in detail in the following text with reference to the exemplary embodiment illustrated in the attached figure, in which.

The exemplary embodiment of the invention described in the following text will be used to illustrate only those medical phenomena which are manifested in the frequency range up to 16 Hz. In an electroencephalogram, the brain currents from 20 signal channels are normally presented. For simplicity, the invention will be explained using the record of predominantly only one channel, for example in the track $FP_2$-$F_8$. The invention can, of course, be applied to all tracks since the point of origin of the signals, that is to say the specific track, is irrelevant for the signal processing described in the following text. The doctor compares the presentation of the signal with the recorded track, and draws medical conclusions from this.

Figure 1:
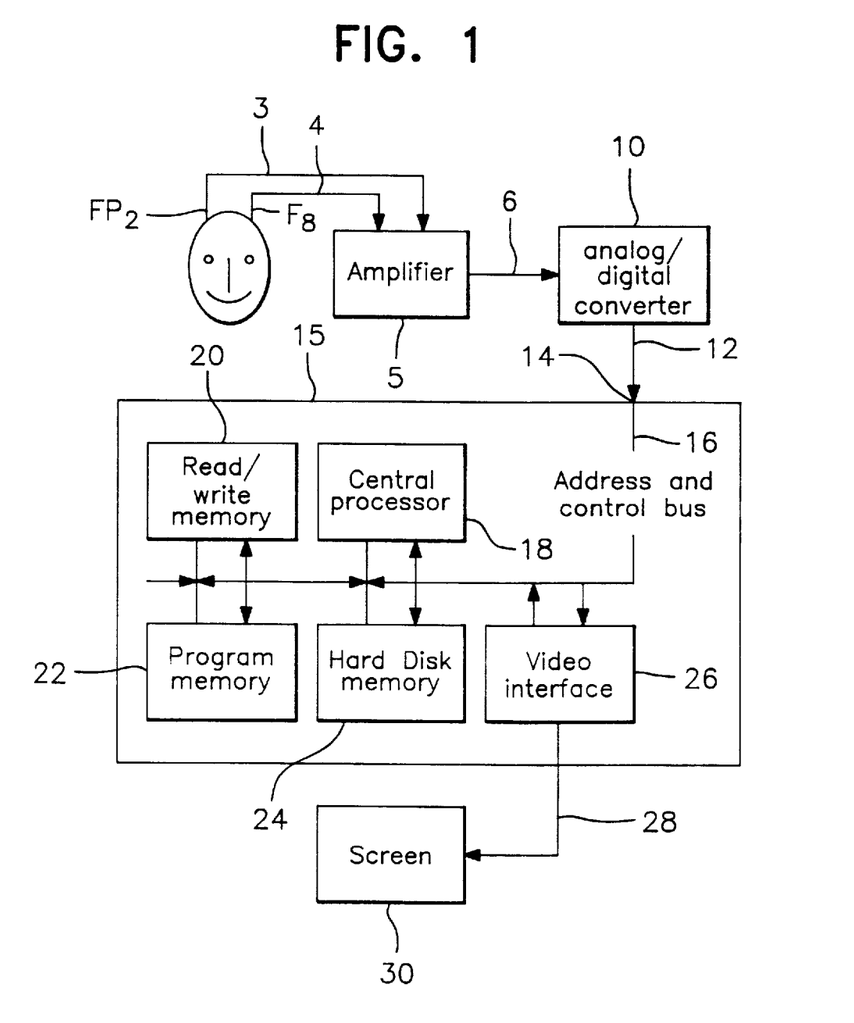
FIG. 1 shows a block diagram of a device which is suitable for carrying out the method according to the invention.

Electrodes are attached in a normal manner to the top of the skull of a patient, at the pick-up points $FP_2$ and $F_8$, and the electrical leads 3, 4 connected to the electrodes are connected to the associated inputs of an amplifier 5.

Figure 2:
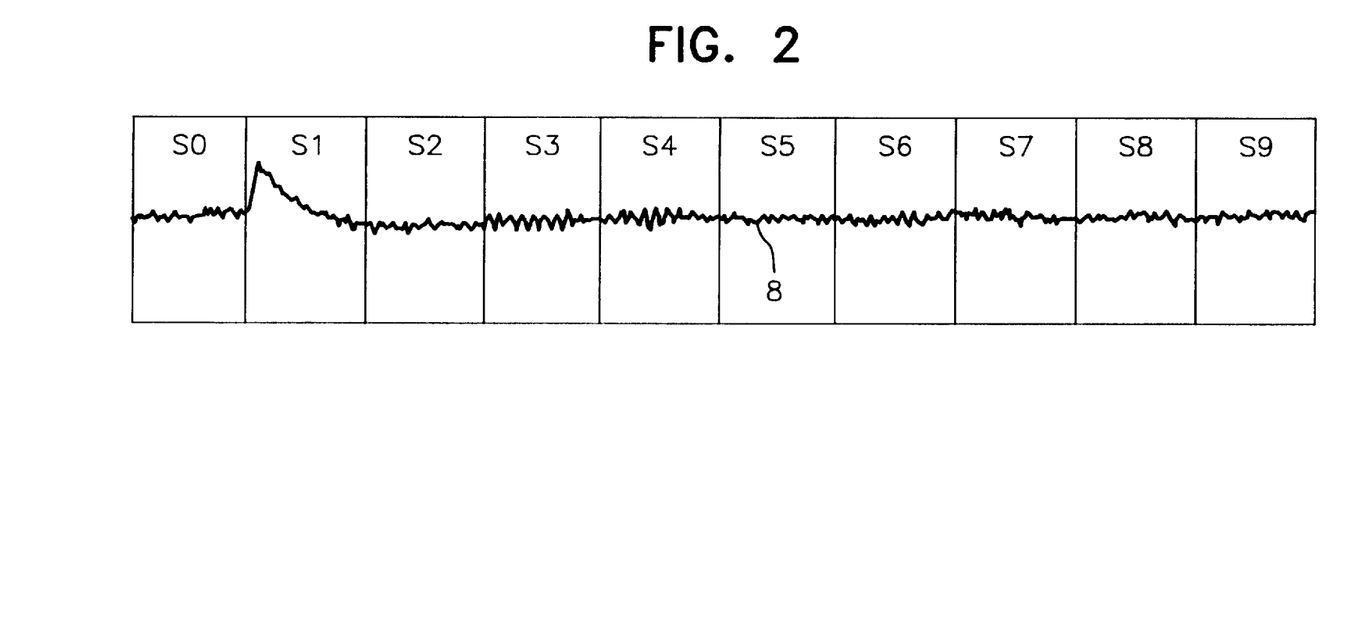
FIG. 2 shows an electroencephalogram of the track $FP_2$-$F_8$ recorded over a time interval of 10 s.

In a conventional display, the amplifier would cause a curve 8 to be displayed on a downstream indicator unit, which is not illustrated, as is shown in FIG. 2 for the first 10 s of the record. The complete time interval of the record would be about 210 seconds, that is to say about 3.5 minutes. The time units associated with the first 10 seconds are indicated in FIG. 2 by S 0 . . . S 9.

The amplified analog signal 8 is fed from the amplifier 5 via an output line 6 to an analog/digital converter 10 which converts the recorded analog signal into 8-bit data words. To this end, the analog/digital converter 10 contains a sample generator which samples the signal, arriving in analog form, at a sampling frequency of 128 Hz, the data word being formed for each sample from the amplitude value of the analog signal. Thus, a data word appears for each sampling time and at a frequency of 128 Hz on the 8-wire output line 12, is fed in bit-parallel form to the input connection 14 of an evaluation device 15 and contains, in coded form, the amplitude value of the sampled, amplified signal 8.

The evaluation device 15 has a central processor 18, a first memory 24 which may be a hard disk memory, a program memory 22, a second memory 20 as a read/write memory and a video interface 26 whose inputs and outputs are connected to an address and control bus 16. The video interface 26 has a further output line 28, which leads to an indicating device 30 having a screen.

Controlled by the central processor 18, the bit-parallel data words passed in serial form from the output line 12 to the address and control bus 16 are saved at successive addresses in a first memory 24. Each address in the first memory thus represents the sampling time at which the data word was generated by the analog/digital converter 10.

A transformation program, which extracts the associated frequencies and amplitudes from a stream of data words, is stored in the program memory 22. Such a program may represent, for example, a Fourier transformation. In the present case, the program represents the maximum entropy method as is explained, for example, by W. H. Press et al. in "Numerical Recipes of the Art of Scientific Computing", Cambridge University Press, 1988, pages 572–576.

Once all the 26,880 data words generated over the recording time interval of 210 seconds have been saved in the first memory 24, they are transformed section-by-section under the control of the central processor 18 and with the aid of the scheme stored in the program memory 22, and the result of the transformation is saved in the second memory 20 at the addresses assigned to the second S 0.

Saving section-by-section in this case means that all 128 data words produced during the second S 0 (FIG. 2) are transformed and saved first of all, that the data words produced during the second S 1, for example, are transformed, and are saved at the address assigned to the second S 1, in the second step, as so on. A set of intermediate data words noted in the second memory is thus obtained from the set of data words.

In the second memory 20, the addresses assigned to the sampling second S 0 are unambiguously assigned to the frequencies f=0 Hz . . . f=16 Hz. For example, an intermediate data word which is associated with the frequency 1 Hz and is obtained from the transformation of the data words from S 0 is saved in the second memory, at the address associated with the frequency 1 Hz. The intermediate data words which result from the transformation of the data words from the sampling second S 1 are saved in a corresponding manner in the second memory at addresses which once again correspond unambiguously to the frequencies f=0 . . . 16 Hz, but now for S 1, to be precise for each intermediate data word at the address associated with its frequency. Each intermediate data word contains a coded value proportional to an amplitude. An address list, to which the central processor 18 has access, is for this purpose saved at a suitable point in one of the units 18, 20, 22, this address list containing the addresses associated with the frequencies for each of the 210 sampling seconds.

Figure 3:
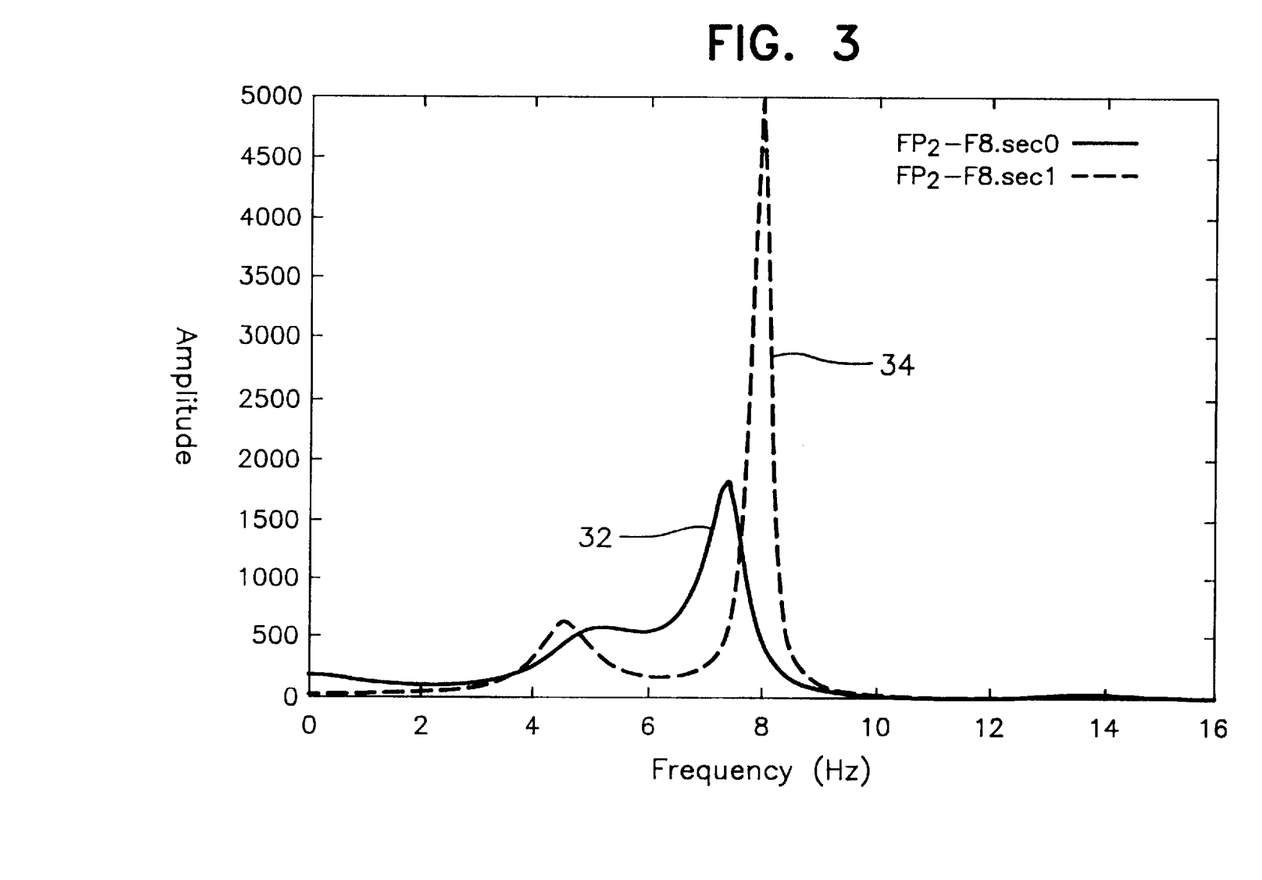
FIG. 3 shows a second spectrum of the seconds zero and one from the record in FIG. 2.
Figure 4:
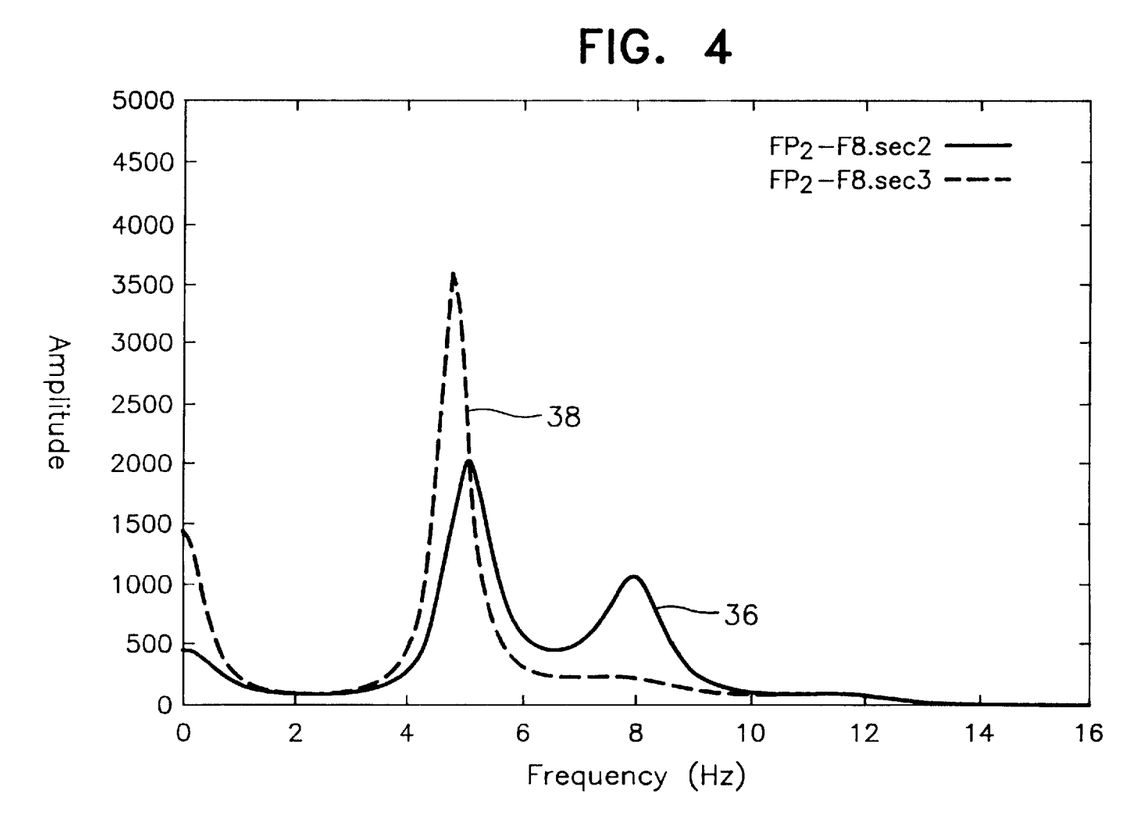
FIG. 4 shows a second spectrum, similar to FIG. 3, from the seconds 2 and 3 in the record in FIG. 2.

If, for example, it is now desired to display the content of the second memory in an amplitude/frequency graph on the indicating device 30, the seconds spectra illustrated in FIG. 3 would be obtained for the seconds S 0 and S 1, and the seconds spectra illustrated in FIG. 4 for the seconds S 2 and S 3.

As indicated in FIGS. 3 and 4, the seconds spectra for the seconds S 0 and S 2 are illustrated by solid lines, and those for the seconds S 1 and S 3 by dashed lines. It can be seen that, in S 0, the curve 32 has an amplitude maximum at about 5.2 Hz, and a further, higher amplitude maximum at about 7.5 Hz. In S 1, the curve 34 shows an amplitude maximum at about 4.5 Hz and a very much higher amplitude maximum at 8 Hz. For S 2, the curve 36 shows an amplitude maximum at about 5 Hz, and a further at 8 Hz, and the curve 38 for S 3, finally, has an amplitude maximum at about 4.7 Hz and a small maximum at about 8 Hz. There is also a third maximum in the seconds spectra for the seconds 2 and 3 in the region of 11.4 Hz.

In order to improve the evaluation of the analog signal S, particularly in the boundary regions between the individual seconds in the sampling time interval, the sections of data words on which the transformation is carried out can be designed such that these sections cover the said boundary regions.

Figure 5:
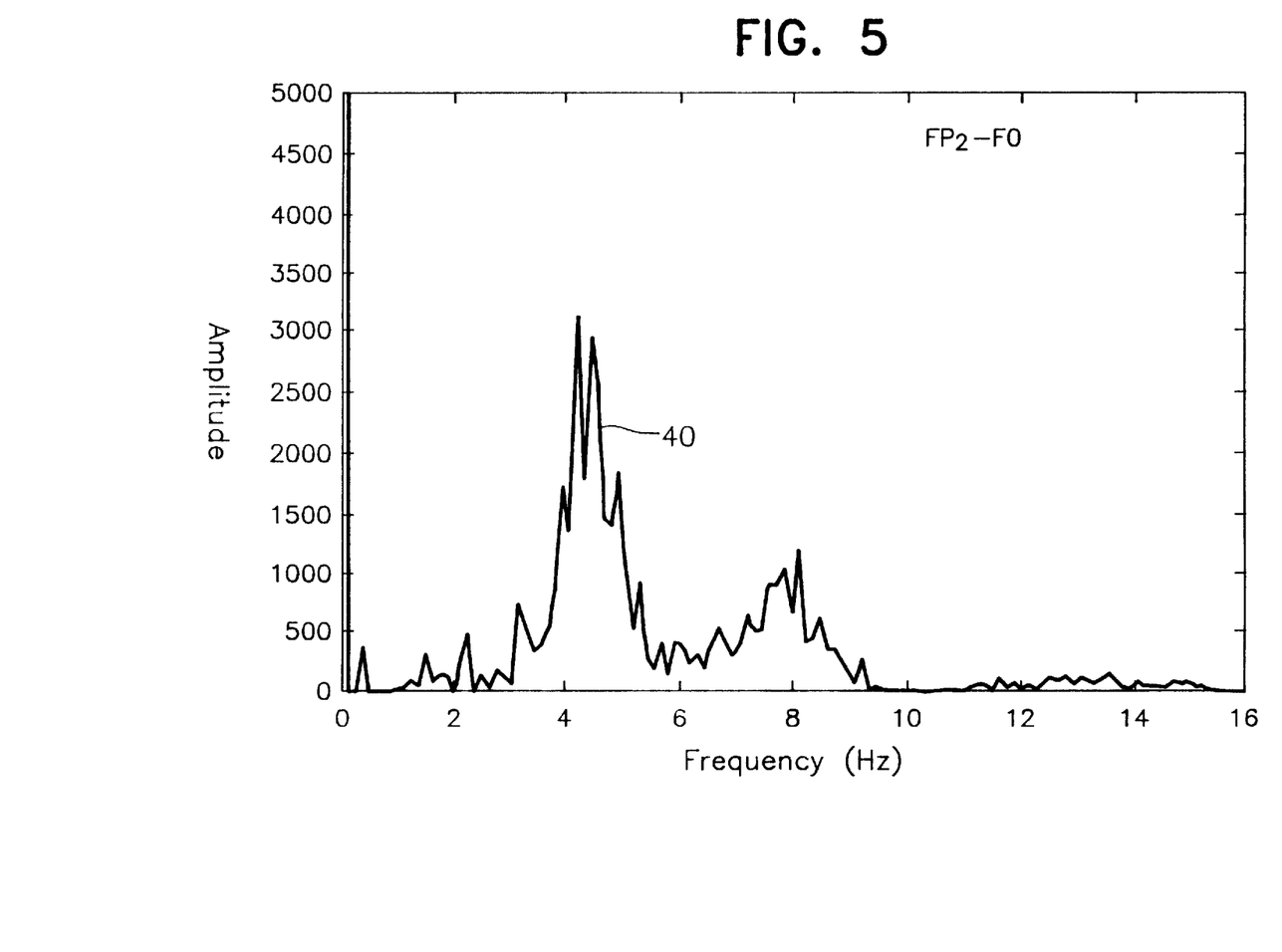
FIG. 5 shows a non-filtered sum spectrum from the record in FIG. 2, but over a time interval of 210 s.

In order to obtain a first medically meaningful representation of the record according to the analog signal 8, a sum spectrum is produced from the contents of the second memory in the following manner: first of all, the magnitudes of the intermediate data words for each second section in the second memory, that is to say for each address section relating to S 1 . . . S 210, are compared to determine those intermediate data words whose value is greater than that of the two adjacent intermediate data words. In other words, the central processor 18 determines the amplitude maxima in each second section. Each maximum intermediate data word determined in this way is marked by the central processor 18, for example by setting an additional flag bit in the intermediate data word. The following averaging process is then carried out in an arithmetic unit (which is not illustrated separately) in the central processor 18 for each frequency to which an address in the second memory area is assigned: the sum of all the amplitudes of the marked intermediate data words associated with one frequency is multiplied by the number of marked intermediate data words associated with this frequency and is divided by the number of sampling seconds (210). In a third memory area of the read/write memory 20, the mean value data words obtained in this way are saved at memory addresses which are unambiguously assigned to the frequency. The mean value date words and signals corresponding to their addresses from the third memory area of the read/write memory 20 are passed under the control of the central processor 18 via the video interface 26 to the indicating device 30. A curve 40, which is shown in FIG. 5, appears on the associated screen, as a amplitude/frequency graph. The amplitude value of the associated mean value data word appears on this curve, for each frequency.

As can be seen from FIG. 5, the curve 40 is distinguished by a large number of peaks, some of which are very sharp. To make it easier for the doctor to evaluate this, the middle data words from the third memory area are passed via a low-pass filter, and are only then fed via the address and control bus 16 to the video interface 26, as a result of which the curve 40 is smoothed to the sum curve 42 illustrated in FIG. 6. Apart from a DC element on the branch 41 of the curve 42 in the frequency band below 1.5 Hz, the observer sees a first relative maximum 44 at about 4 Hz and a, smaller, second maximum 46 at about 8 Hz. A barely perceptible third maximum 50 may be noted at about 15 Hz.

Figure 6:
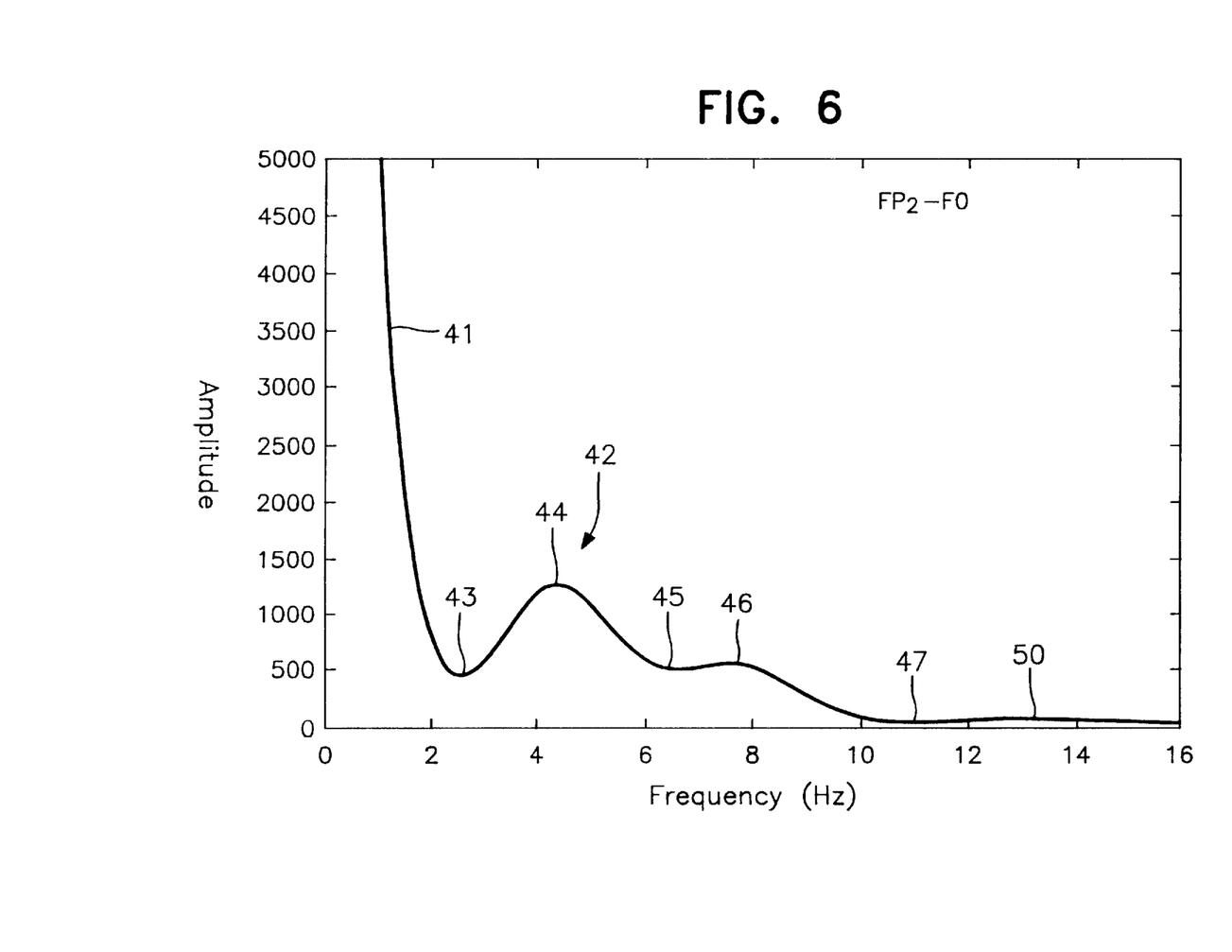
FIG. 6 shows the filtered sum spectrum from FIG. 5.

Medically, this result means that the patient investigated has considerable brain activity at 4 Hz, and less at 8 Hz. Above all, the first maximum 44 is significantly lower than the frequency band of 8–13 Hz of alpha waves, which indicates a pathological situation in the brain section of the patient, which corresponds to the position recorded.

In order to increase even further the usefulness of the presentation of the analog signal 8 for the clinician, a frequency drift display of the analog signal is produced with the assistance of the data words stored in the first memory 24, and this allows the extracted frequencies to be compared with the medical division into the already mentioned alpha waves (frequency band from 8 to 13 Hz), the beta waves (frequency above 13 Hz), the delta band (frequencies below 3 Hz) and the theta band (frequencies of 4–7 Hz).

Specifically, as can be seen from FIG. 6, increased brain activity, represented by the maxima 44, 46 and 50 takes place within the frequency bands whose boundaries are indicated by the minima located between the maxima.

For example, there is a relative minimum 43 at about 2.5 Hz, a further minimum 45 at about 6.2 Hz, and a third minimum 47 at about 11 Hz. The central processor 18 thus, for example, uses the already mentioned comparitor to find from the third memory area in the read/write memory 20 the frequencies at which relative minima may occur in the mean value data words.

Figure 7:
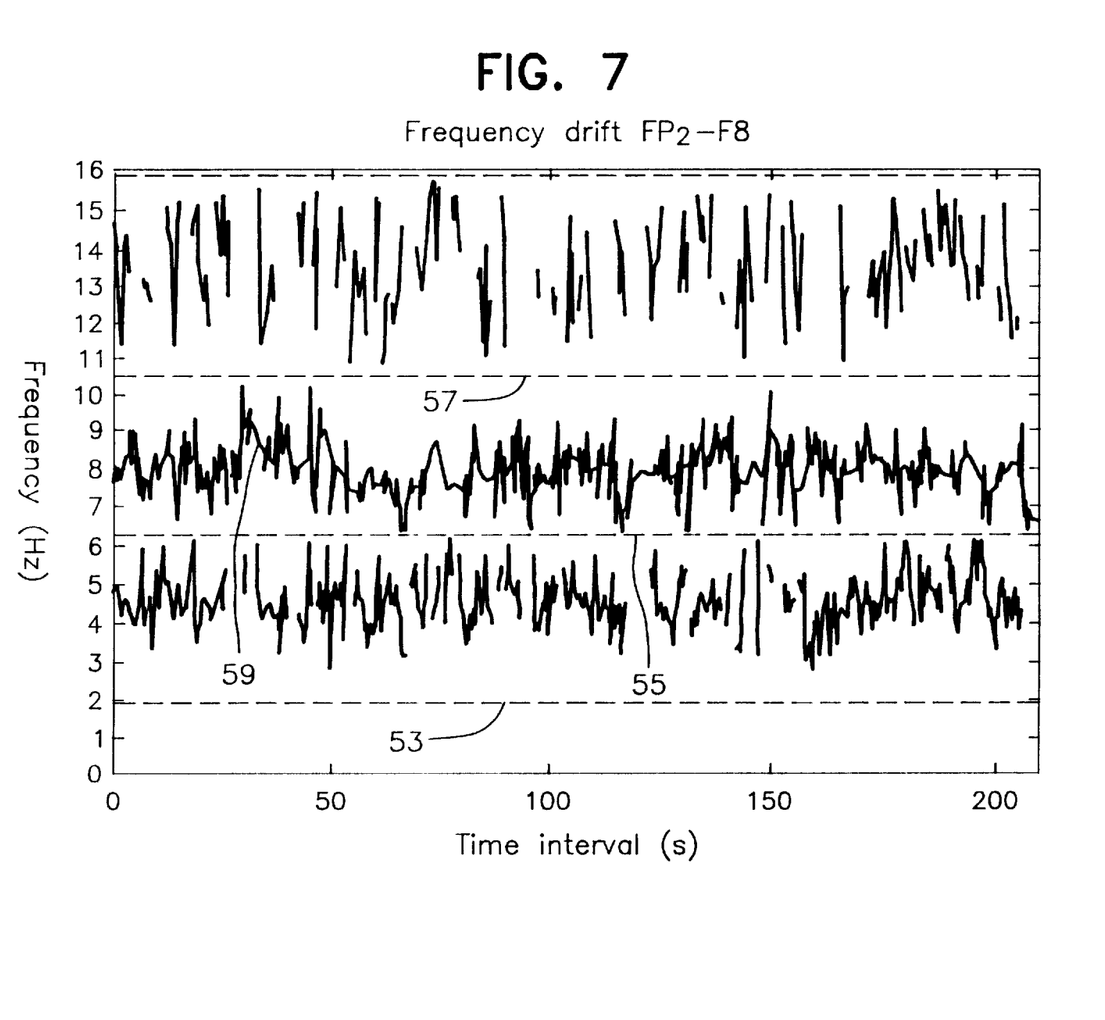
FIG. 7 shows a frequency drift presentation from the record in FIG. 2; but over a time interval of 210 s.

The associated frequencies $F_{min}$ and the signals corresponding to them are passed via the video interface 26 to the indicating device 30 and are displayed as horizontal lines 53, 55, 57 on the screen in a graph whose abscissa is the overall recording time interval in seconds and whose ordinate is the frequency in Hz.

Furthermore, the central processor 18 accesses the second memory 20 and, within each second section, checks all the intermediate data words for the presence of the marking (which, as mentioned, indicates a relative maximum). The addresses associated with the marked intermediate data words (which represent a frequency) are plotted on the graph in FIG. 7 as (frequency) points associated with the respective second section, by feeding the respective signals to the indicating device 30. The indicator unit 30 thus receives one or more frequency signals for each second section S 0, S 1 . . . S 210 in the second memory area, each of which is allocated to an intermediate data word representing an amplitude maximum. The indicating device 30 enters these frequency signals on the graph illustrated in FIG. 7. A number of interrupted curve families can be seen within the individual frequency bands, indicated by the dashed lines 53, 55, 57 over the recording time interval of 210 seconds.

To improve the clarity particularly in the region of the basic rhythm in the graph in FIG. 7, the frequency signals that occur in this frequency band are passed separately via a low-pass filter, and the output signal from the low-pass filter is plotted by the indicating device in the frequency range between the curves 55 and 57.

This results in the integration curve 59 illustrated. The basic rhythm is defined by that frequency interval between the curves 53, 55, 57 in which the number of frequency signals that occur is a maximum.

Figure 8:
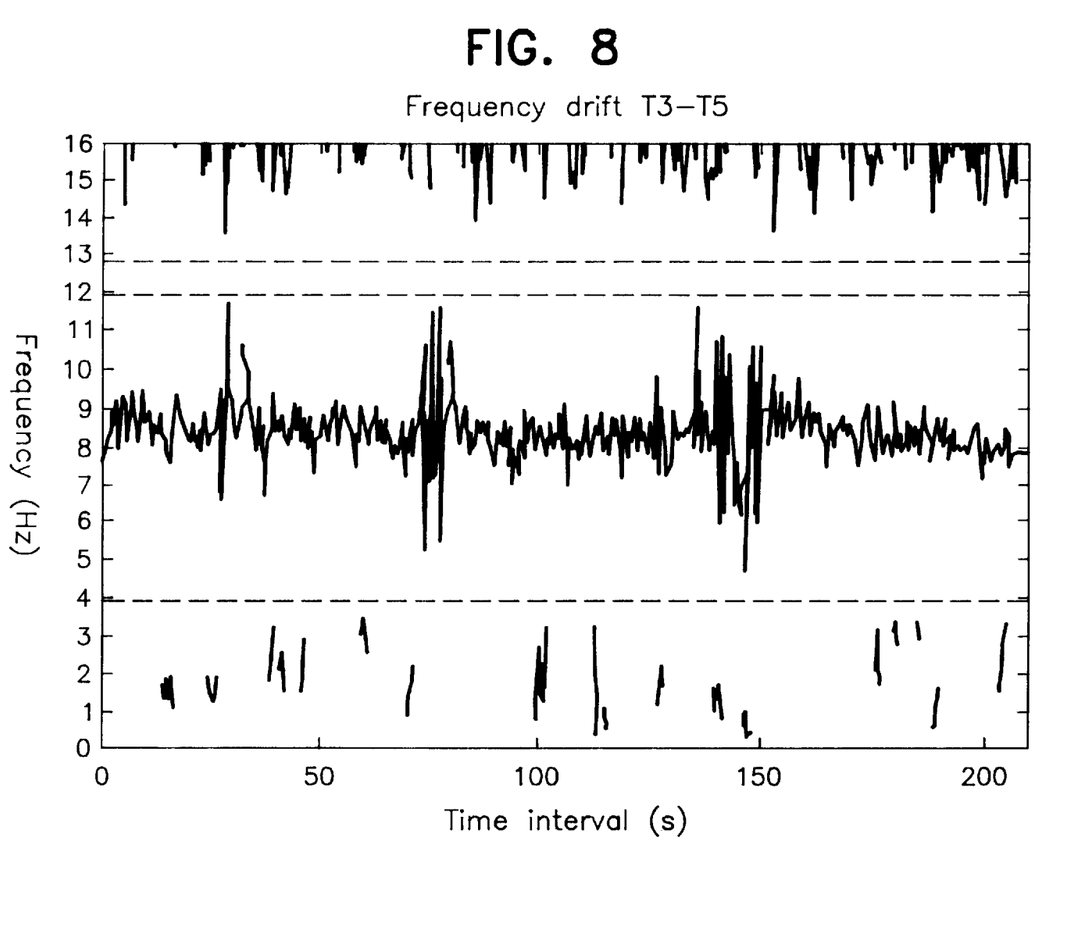
FIG. 8 shows a frequency drift presentation similar to FIG. 7 but from a different track.

From the frequency drift graph for the track $FP_2$-$F_8$ in FIG. 7, the doctor can see that the basic rhythm associated with the alpha wave band is, in general, slightly slowed down on the part of the hemisphere of the patient being detected, since the basic rhythm of the brain activity is in this case in the frequency range from about 6.5 to about 10.5 Hz and the integration curve is very frequently under 8 Hz while the basic rhythm in a healthy person may be expected in the alpha band from 8 to 13 Hz. Furthermore, the doctor can see from this frequency drift graph that the patient being examined presents continuous epileptogenic foci of medium severity in the right, temporal lobe. In another track T3-T5 (FIG. 8), it can be seen that there is no activity in the region from 4 to 7 Hz. The basic rhythm has also been slightly slowed down, and the activity in the region below 4 Hz may be ascribed to eye-movement artifacts. By comparing the frequency drift graphs for different brain regions, the doctor can distinguish between a focus and a generalized phenomenon.

Finally, the contents of the second memory can also be presented as amplitude drift, which allows the doctor to make further deductions about the brain activity. To do this, the central processor 18 once again accesses the second memory 20 and determines second-by-second, that is to say first for S 0 then for S 1 etc., those intermediate data words which are within a given frequency range, that is to say a given address subsection.

Each address subsection is defined by the frequency interval between two relative minima in the sum spectrum in FIG. 6, that is to say by the frequency boundaries 53, 55, 57 in FIG. 7. In the case of an EEG record on the track T3-T5 (FIG. 8), the frequency intervals are at 3.8 . . . 11.9 Hz and at 11.9 . . . 12.8 Hz. For each of the intermediate data words already found in each frequency interval and having a marking (maximum) the central processor 18 forms a signal proportional to the value of this word and sends this signal to the indicating device 30. The indicating device 30 enters these signals on a graph according to FIG. 9, whose abscissa once again shows the total recording time interval of 210 seconds and whose ordinate shows the amplitudes in $\mu$ volts, for each frequency range with respect to a specific zero line. The family of curves 64 then appears over the entire recording time interval (S 1 . . . S 20) over the reference line 62 relating to the frequency band 11.9 . . . 12.8 Hz. This family of curves 64 shows, at 66, 68 and 70, so-called amplitude suppressions, which are characterized by amplitude values of virtually zero $\mu$ volts. A comparison of the timing of the amplitude suppressions 66, 68 and 70 with the record shows that the patient opened his eyes during the associated recording times. The triple Berger effect at the recording times of 30, 70 and 140 seconds may thus medically be assessed as being positive.

Figure 9:
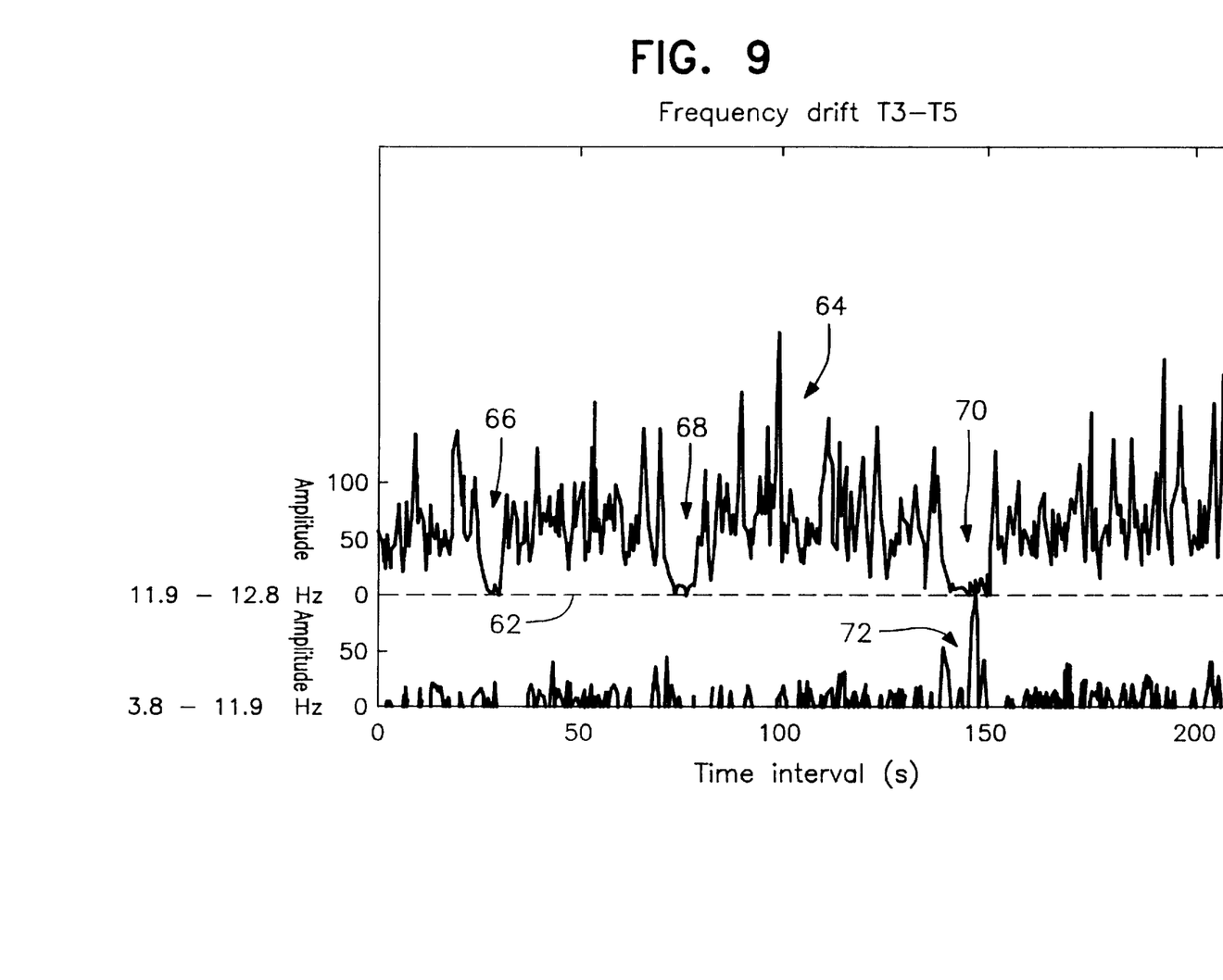
FIG. 9 shows an amplitude drift presentation.

Finally, the amplitude drift graph in FIG. 9 shows high-amplitude eye-movement artifacts 72 in the frequency band from 3.8–11.9 Hz at the recording times from 140–150 s.

It can be seen that the type of processing for EEG signals described above using the evaluation device 15 and the analog/digital converter 10 allows displays of brain activity to be obtained in the indicating device 30 which allow the doctor to make a medical assessment easily and directly.

Frequency-linked phenomena, such as the basic rhythm, pathologically slow activity or specific artifacts are described individually in separate frequency bands, can be evaluated individually by the doctor and do not interfere with one another as in a conventional EEG.

I claim:

1. Method for evaluating electrically detected brain activity, in which a signal picked off from the top of the skull over a given time interval is converted at a given sampling frequency into a sequence of data words from which the amplitudes and the frequency associated with each amplitude are extracted in accordance with a predetermined scheme (Fourier transformation or the like) in an arithmetic unit, in such a manner that intermediate data words are formed, each of which represents an amplitude and is saved at a memory address which is governed by the frequency associated with the intermediate data word, furthermore, of all the intermediate data words, those maximum intermediate data words being determined which are a relative maximum, and in such a manner that a mean value is formed from the maximum intermediate data words for each frequency and all the mean values are passed with the associated frequency to an indicating device (30) for display using a frequency/amplitude graph.

2. Method according to claim 1, characterized in that, in order to form the mean value, the sum of the maximum intermediate data words present per frequency is multiplied by the number of said words and is divided by a given reference variable.

3. Method according to claim 1, characterized in that each mean value is temporarily saved, as a mean value data word, at an address governed by the associated frequency.

4. Method according to claim 1, characterized in that, with the time interval being subdivided into a number of time units, the extraction is carried out for each time unit (sampling second), the intermediate data words formed for each time unit being saved at memory addresses which are defined unambiguously for the time unit by the frequency associated with the intermediate data word, and in that the reference variable is the number of time units in the time interval.

5. Method according to claim 1, characterized in that the mean value data words fed to the indicating device (30) are passed via a low-pass filter.

6. Method according to claim 1, characterized in that, of the mean value data words, those are determined which are a relative minimum, and in that the frequency associated with each minimum mean value data word is fed to the indicating device (30) for separate display.

7. Method according to claim 1, characterized in that the frequencies of the maximum intermediate data words in each time unit are determined and are passed to the indicating device (30) to provide a frequency drift display.

8. Method according to claim 7, characterized in that the frequencies which are in the region of the basic rhythm are passed via a low-pass filter, and the output of the low-pass filter is fed to the indicator unit (30).

9. Method according to claim 1, characterized in that, for each time unit, all the intermediate data words within a frequency interval are passed to the indicator unit (30) to provide an amplitude drift display, the frequency interval being defined by the frequency difference between two minimum mean value data words.

10. Device for evaluating electrically detected brain activity for carrying out the method according to claim 1, having an analog/digital converter (10) in which a signal (8) picked off from the top of the skull over a given time interval is converted at a given sampling frequency into a sequence of data words, having an evaluation device (15) whose address and control bus (16) feeds the data words from the analog/digital converter (10) to a first memory (24), a predetermined scheme (Fourier transformation or the like) being stored in a program memory (22) in the evaluation device (15), by means of which scheme a central processor (18), which is provided in the evaluation device (15) and contains an arithmetic unit, extracts from the data words stored in the first memory (24) the amplitudes as well as the frequency associated with each amplitude and saves the results in a second memory (20) in such a manner that the addresses which are assigned to the frequencies have intermediate data words written to them, each of which represents an amplitude, the arithmetic unit determining those intermediate data words which are a relative maximum and forming a mean value for each frequency from the maximum intermediate data words, and the central processor (18) feeding all the mean values, with the associated frequencies, via the address and control bus (16) to an indicating device (30).

11. Device according to claim 10, characterized in that the indicating device (30) has a screen and is coupled to the address and control bus (26) via a video interface (26).

12. Device according to claim 10, characterized in that, in order to form the mean value, the arithmetic unit multiplies the sum of the maximum intermediate data words present per frequency by the number of said data words, and divides it by a given reference variable.

13. Device according to claim 10, characterized in that the central processor (18) temporarily saves each mean value as a mean value data word at an address, governed by the associated frequency, in a third memory.

14. Device according to claim 10, characterized in that the evaluation device (15) has a low-pass filter via which the central processor (18) feeds the mean value data words to the indicating device (30).

15. Device according to claim 10, characterized in that the arithmetic unit determines from the mean value data words those which are a relative minimum, and in that the central processor (18) feeds to the indicating device (30) the frequency associated with each minimum mean value data word.

16. Device according to claim 10, characterized in that, with the time interval being split into a number of time units, the arithmetic unit carries out the extraction for each time unit (sampling second) and the central processor (18) saves the intermediate data words formed for each time unit at memory addresses in the second memory (20), which is are unambiguously defined for the time unit by the frequency associated with the intermediate data word, and in that the reference variable is the number of time units.

17. Device according to claim 10, characterized in that the arithmetic unit passes, for each time unit, all the intermediate data words within a frequency interval to the indicating device (30), the frequency interval being governed by the frequency difference between two minimum mean value data words.

18. Device according to claim 10, characterized in that the central processor (18) has a list of memory addresses with associated frequencies.

19. Device according to claim 10, characterized in that the arithmetic unit passes to the indicating device (30), for each time unit and via a low-pass filter, all those frequencies which are within a frequency interval associated with the basic rhythm.

* * * * *